United States Patent [19]
Hirsch et al.

[11] Patent Number: 5,250,539
[45] Date of Patent: Oct. 5, 1993

[54] HEXAHYDROBENZO[F]QUINOLINONES

[75] Inventors: Kenneth S. Hirsch; Charles D. Jones, both of Indianapolis, Ind.

[73] Assignee: Eli Lilly and Company, Indianapolis, Ind.

[21] Appl. No.: 780,166

[22] Filed: Oct. 21, 1991

Related U.S. Application Data

[63] Continuation-in-part of Ser. No. 748,134, Aug. 21, 1991, abandoned.

[51] Int. Cl.$^5$ ............... C07D 221/14; C07D 295/073; A61K 31/44
[52] U.S. Cl. .................... 514/290; 546/101; 564/428; 548/578
[58] Field of Search .............. 546/101; 514/290

[56] References Cited

U.S. PATENT DOCUMENTS

| | | | |
|---|---|---|---|
| 4,511,569 | 4/1985 | Smith et al. | 514/290 |
| 4,749,791 | 6/1988 | Aschwanden et al. | 546/101 |
| 4,859,681 | 8/1989 | Rasmusson | 514/284 |
| 4,888,336 | 12/1989 | Holt | 514/278 |
| 5,120,742 | 6/1992 | Rasmusson | 514/284 |
| 5,120,840 | 6/1992 | Weintraub | 540/28 |

FOREIGN PATENT DOCUMENTS

| | | |
|---|---|---|
| 291245 | 11/1988 | European Pat. Off. |
| 2207135 | 1/1989 | United Kingdom |

OTHER PUBLICATIONS

Horii I, Chem Abs 62, 10405b (1964).
Horii II, Chem Abs 61, 14635h (1964).
Kadohama, Cancer Research 44, 4947 (1984).
Holt, J. Med Chem 33, 943 (1990).
Kadohama, AACH Abstracts, Mar. 1984, vol. 25, p. 209.
Brooks, The Prostate 9, 65 (1986).
Huggins, Cancer Res 1, 293 (1941).
Imperato-McGinley, Science, 186, 1213 (1974).
Andriole, The Prostate 10, 189-197 (1987).
Rittmaster, J. Clin Endrocrine & Metal 65, p. 188 (1987).
Bruchovsky, J. Biol. Chem 243, 2012 (1968).
Itami, J. Investigative Dermatol. 94, 150 (1990).
Hamilton, American J. Anat. 71, 451 (1972).
Takayasu, J. Clin. Endrocin Metab 34, 1098 (1972).
Bingham, J. Endrocrin 57, 111 (1973).
Mooradian, Endocrine Reviews 8, 1 (1972).
Hay, J. Endrocrin. 79, 29 9 (1978).
Rassmusson, J. Med Chem 29, 2298 (1986).
Stinson, Chem & Erg News Jun. 29, 1992 p. 7.
Lamberigts, J. Clin. Endrocin 48, 924 (1979).
ATCC Catalogue of Cell Liens, 1988, p. 159.
Metcalf, Trends in Pharm. Sci 10, 1989, p. 491.
Moore, J. Biol. Chem 251, 5895 (1976).
Moore J. Biol. Chem 250, 7168 (1975).
Leshin, J. Clin. Inves. 62, 503 (1978).
Williams, "Textbook of Endrocrinolog",6th Edition (1981) 1080–1098.
Brooks Endocrinology, 109, 830 (1981).
Wenderoth, Endocrinology 113, 569 (1983).
Schweikert, J. Clin Endocrinol Metal 79, 29 (1978).
Wilson, J. Clin. Investigation 48, p. 371 (1969).
Bach et al., *J. Med. Chem.*, 23, 812–814 (1980).
Cannon et al., *J. Med. Chem.*, 22, 341–347 (1979).
Cannon et al., *J. Med. Chem.*, 23, 1–5 (1980).
Cannon et al., *J. Med. Chem.*, 19, 987–993 (1976).
Cannon et al., *J. Med. Chem.*, 29, 2529–2534 (1986).
Cannon et al., *J. Med. Chem.*, 27, 190–195 (1984).
Wikstrom et al., *J. Med. Chem.*, 25, 925–931 (1982).

(List continued on next page.)

*Primary Examiner*—Mark L. Berch
*Attorney, Agent, or Firm*—Joseph A. Jones; Leroy Whitaker; John C. Demeter

[57] ABSTRACT

The invention relates to 1,2,3,4,5,6-hexahydrobenzo[f]quinolin-3-ones, pharmaceutical formulations containing those compounds, and their use as steroid 5α-reductase inhibitors.

36 Claims, No Drawings

OTHER PUBLICATIONS

Cannon et al., *J. Pharm. Sci.*, 74, 672–675 (1985).
Kiguchi et al., *Heterocycles*, 18, 217–220 (1982).
Ninomiya et al., *J. Chem. Soc., Perkin Trans 1*, 2967–2971 (1983).
Ninomiya et al., *J. Chem. Soc., Perkin Trans 1*, 2911–2917 (1984).
Cannon et al., *Synthesis*, 6, 494–496 (1986).
Horii et al., *Chem. Pharm. Bull.*, 16, 668–671 (1968).
Horii et al., *Chem Pharm. Bull.*, 1227–1236 (1966).
Costall et al., *J. Pharm. Pharmacol.*, 34, 246–254 (1982).
Petrow, *The Prostate*, 9:343–361, published by Alan R. Liss, Inc. (1986).
Kadohama et al., 75th Annual Meeting of AACR, Abstracts, vol. 25, 827 (1984).
Petrow et al., *J. Pharm. Pharmacol.* 36:352–353 (1984).

HEXAHYDROBENZO[F]QUINOLINONES

This application is a continuation-in-part of application Ser. No. 07/748,134 filed Aug. 21, 1991, now abandoned.

BACKGROUND OF THE INVENTION

The present invention relates to hexahydrobenzo[f]quinolinones, pharmaceutical formulations containing those compounds and their use as steroid 5α-reductase inhibitors.

It is generally known that certain undesirable physiological conditions such as benign prostatic hyperplasia, male pattern baldness, acne vulgaris, hirsutism and prostatic cancer are androgen mediated conditions dependent on 5α-dihydrotestosterone (DHT).

The enzyme 5α-reductase mediates the conversion of testosterone to the more potent androgen DHT locally, in the target organ. It has been postulated, and demonstrated, that inhibitors of 5α-reductase should block the formation of DHT and bring about amelioration of the above undesirable physiological conditions.

Compounds reportedly useful for inhibiting 5α-reductase are generally steroid derivatives such as the azasteroids in Rasmusson, et al., *J. Med. Chem.*, 29, (11), 2298-2315 (1986); and benzoylaminophenoxy-butanoic acid derivatives such as those disclosed in EPO 291 245.

Certain hexahydrobenzo[f]quinolinone compounds are known. See, for example, GB 2,207,135; and U.S. Pat. No. 4,749,791. Both GB 2,207,135 and U.S. Pat. No. 4,749,791 do not disclose a pharmaceutical use for the hexahydrobenzo[f]quinolinones disclosed therein except as intermediates for the preparation of other compounds said to have pharmaceutical utility. U.S. Pat. No. 4,511,569 discloses that certain tricyclic lactams and derivatives are useful in increasing cardiac contractility. The references do not suggest the hexahydrobenzo[f]quinolinones of the present invention would be useful as steroid 5α-reductase inhibitors.

Accordingly, it is one object of the present invention to provide novel hexahydrobenzo[f]quinolinones which are potent selective steroid-5α-reductase inhibitors useful in the treatment of benign prostatic hyperplasia, male pattern baldness, acne vulgaris, hirsutism and prostatic cancer.

A further object of the present invention is to provide therapeutic compositions for treating said conditions.

Still another object is to provide methods for treating said conditions.

Other objects, features and advantages will become apparent to those skilled in the art from the following description and claims.

SUMMARY OF THE INVENTION

The present invention provides novel 1,2,3,4,5,6,hexahydrobenzo[f]quinolin-3-ones which are effective steroid 5α-reductase inhibitors.

More specifically, this invention relates to compounds having the Formula

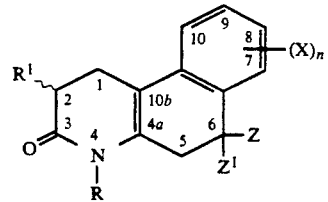

where:
R is hydrogen, $C_1$-$C_4$ alkyl, unsubstituted or substituted phen($C_1$-$C_4$)alkyl;
Z and $Z^1$ are independently selected from hydrogen and $C_1$-$C_4$ alkyl;
$R^1$ is hydrogen or $C_1$-$C_4$ alkyl;
n is 1 or 2;
X is hydrogen, halogen, $NO_2$, cyano, $CF_3$, $C_1$-$C_6$ alkyl, $C_1$-$C_6$ alkoxy, carboxy, $C_1$-$C_6$ alkoxycarbonyl, amino, $C_1$-$C_4$ alkylamino, $C_1$-$C_4$ dialkylamino, amido, $C_1$-$C_4$ alkylamido, $C_1$-$C_4$ dialkylamido, mercapto, $C_1$-$C_6$ alkylthio, $C_1$-$C_6$ alkylsulfinyl, $C_1$-$C_6$ alkylsulfonyl, or a group —A—$R^2$ where A is $C_1$-$C_6$ alkylene, $C_2$-$C_6$ alkenylene or $C_2$-$C_6$ alkynylene; and $R^2$ is halogen, hydroxy, $CF_3$, $C_1$-$C_6$ alkoxy, carboxy, $C_1$-$C_6$ alkoxycarbonyl, amino, $C_1$-$C_4$ alkylamino, $C_1$-$C_4$ dialkylamino, amido, $C_1$-$C_4$ alkylamido, $C_1$-$C_4$ dialkylamido, $C_1$-$C_4$ alkylsulfonylamino, aminosulfonyl or $C_1$-$C_4$ alkylaminosulfonyl; and pharmaceutically acceptable salts thereof; provided that:
(a) when R is hydrogen, X is not hydrogen, halo or methoxy;
(b) when R is methyl, ethyl or benzyl, X is not methoxy; and
(c) when R is methyl, $R^1$ is not methyl.

This invention also provides pharmaceutical formulations which comprising, a compound having the Formula,

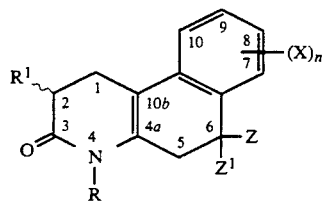

where:
R is hydrogen, $C_1$-$C_4$ alkyl, unsubstituted or substituted phen($C_1$-$C_4$)alkyl;
Z and $Z^1$ are independently selected from hydrogen and $C_1$-$C_4$ alkyl;
$R^1$ is hydrogen or $C_1$-$C_4$ alkyl;
n is 1 or 2;
X is hydrogen, halogen, $NO_2$, cyano, $CF_3$, $C_1$-$C_6$ alkyl, $C_1$-$C_6$ alkoxy, carboxy, $C_1$-$C_6$ alkoxycarbonyl, amino, $C_1$-$C_4$ alkylamino, $C_1$-$C_4$ dialkylamino, amido, $C_1$-$C_4$ alkylamido, $C_1$-$C_4$ dialkylamido, mercapto, $C_1$-$C_6$ alkylthio, $C_1$-$C_6$ alkylsulfinyl, $C_1$-$C_6$ alkylsulfonyl, or a group —A—$R^2$ where A is $C_1$-$C_6$ alkylene $C_2$-$C_6$ alkenylene or $C_2$-$C_6$ alkynylene; and $R^2$ is halogen, hydroxy, $CF_3$, $C_1$-$C_6$ alkoxy, carboxy, $C_1$-$C_6$ alkoxycarbonyl, amino, $C_1$-$C_4$ alkylamino, $C_1$-$C_4$ dialkylamino, amido, $C_1$-$C_4$ alkylamido, $C_1$-$C_4$ dialkylamido, $C_1-C_4$ alkylsulfonylamino, aminosulfonyl or $C_1-C_4$ alkylaminosulfonyl; or a pharmaceutically acceptable salt thereof in association with a pharmaceutically acceptable carrier, diluent, or excipient.

A further embodiment of the present invention is a method for inhibiting $5\alpha$-reductase. More particularly, further embodiments are methods for treating a variety of disorders which have been linked to $5\alpha$-reductase activity in mammals. Included among those disorders are benign prostatic hyperplasia, male pattern baldness, acne vulgaris, hirsutism and prostatic cancer. These methods comprise administering to a mammal in need of $5\alpha$-reductase inhibition, a $5\alpha$-reductase inhibiting dose of a compound having the Formula

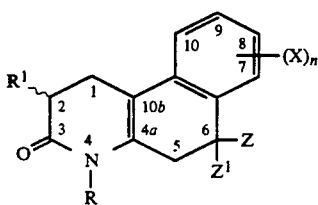

I where:

R is hydrogen, $C_1-C_4$ alkyl, unsubstituted or substituted phen($C_1-C_4$)alkyl;

Z and $Z^1$ are independently selected from hydrogen and $C_1-C_4$ alkyl;

$R^1$ is hydrogen or $C_1-C_4$ alkyl;

n is 1 or 2;

X is hydrogen, halogen, $NO_2$, cyano, $CF_3$, $C_1-C_6$ alkyl, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, mercapto, $C_1-C_6$ alkylthio, $C_1-C_6$ alkylsulfinyl, $C_1-C_6$ alkylsulfonyl, or a group $-A-R^2$ where A is $C_1-C_6$ alkylene $C_2-C_6$ alkenylene or $C_2-C_6$ alkynylene; and $R^2$ is halogen, hydroxy, $CF_3$, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl; or a pharmaceutically acceptable salt thereof.

DETAILED DESCRIPTION OF THE INVENTION

As used herein, the term "alkyl" means a straight or branched alkyl radical having the stated number of carbon atoms. Such alkyl groups include methyl, ethyl, n-propyl, isopropyl, n-butyl, isobutyl, sec-butyl, t-butyl and, where indicated, higher homologs and isomers such as n-pentyl, n-hexyl, 2-methylpentyl and the like.

The term "alkylene" means a bivalent straight chain alkyl radical having the stated number of carbon atoms such as methylene, 1,2-ethanediyl, 1,3-propanediyl, 1,4-butanediyl, 1,5-pentanediyl, 1,6-hexanediyl. Similarly, "alkenylene" means a bivalent unsaturated straight chain hydrocarbon group having the stated number of carbon atoms and a single carbon-carbon double bond such as vinylene, 1-propene-1,3-diyl, 2-propene-1,3-diyl, 2-butene-1,4-diyl, 1-butene-1,4-diyl and the like. Similarly, "alkynylene" means a bivalent straight chain hydrocarbon group having the stated number of carbon atoms and a single carbon-carbon triple bond such as 1,2-acetylenediyl, 1-propyne-1,3-diyl, 2-butyne-1,4-diyl the like.

The term "phen($C_1-C_4$)alkyl" means a one to four carbon, straight or branched chain, alkyl radical monosubstituted with an unsubstituted or substituted phenyl ring where the substituents are the same or different halogen, $C_1-C_4$ alkyl, $C_1-C_4$ alkoxy, amino, $C_1-C_4$ alkylamino or $C_1-C_4$ dialkylamino. Typical phen($C_1-C_4$)alkyl groups include benzyl, 2-pheneth-1-yl, 3-phenprop-1-yl, 4-phenbut-1-yl, 1-pheneth-1-yl, 2-phenprop-1-yl, 2-(4-halophenyl)eth-1-yl, 4-halobenzyl, and the like.

The term "alkoxy" means any of methoxy, ethoxy, n-propoxy, isopropoxy and the like. The term "halogen" and "halo" means any of fluoro, chloro, bromo, and iodo. The term "alkylthio" means any of methylthio, ethylthio, n-propylthio, isopropylthio and the like.

Where a "$C_1-C_4$ dialkylamino" ($-N(C_1-C_4$ alkyl$)_2$) or "$C_1-C_4$ dialkylamido" ($-C(O)N(C_1-C_4$ alkyl$)_2$)substituent is indicated, each alkyl group, independently, has one to four carbon atoms.

The compounds of Formula I may possess, depending upon the $R^1$, Z and $Z^1$ substituents, one or more asymmetric carbon atoms and therefore can exist as individual diastereomers as well as racemates of those diasterreomers. The compounds of the present invention include not only mixtures of two or more of such diastereomers, but also the respective individual isomers.

Preferred compounds of the present invention are those of Formula I where:

R is hydrogen or $C_1-C_4$ alkyl;

Z and $Z^1$ are independently hydrogen or methyl;

$R^1$ is hydrogen or methyl;

n is 1 or 2;

X is halogen, $CF_3$, $C_1-C_6$ alkyl, $C_1-C_4$ alkoxy or $-A-R_2$ where A is $C_1-C_4$ alkylene and $R_2$ is $C_1-C_4$ alkoxycarbonyl; and pharmaceutically acceptable salts thereof; provided that:

(a) when R is hydrogen, X is not hydrogen, halo or methoxy;

(b) when R is methyl or ethyl, X is not methoxy; and (c) when R is methyl, $R^1$ is not methyl.

Most preferred compounds of the present invention are those of Formula I where:

R is hydrogen or methyl;

Z and $Z^1$ are both hydrogen or methyl;

$R^1$ is hydrogen or methyl;

n is 1 or 2;

X is halogen, $CF_3$, or $C_1-C_4$ alkyl; and pharmaceutically acceptable salts thereof; provided that:

(a) when R is hydrogen, X is not halogen;

(b) when R is methyl, $R^1$ is not methyl.

As mentioned above, the invention includes pharmaceutically acceptable salts of the compounds defined by the above formula. Although generally neutral, a particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like, as well as salts derived from nontoxic basic organic amines, such as aliphatic and aromatic amines, aliphatic diamines, hydroxy alkylamines, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, methylamine, diethylamine, ethylenediamine, cyclohexylamine, ethanolamine, and the like. The potassium and sodium salt forms are particularly preferred.

The compounds of the present invention, or their precursors, are prepared using procedures known to those of ordinary skill in the art. These compounds of the present invention or their precursors are preferably synthesized according to the following Scheme 1.

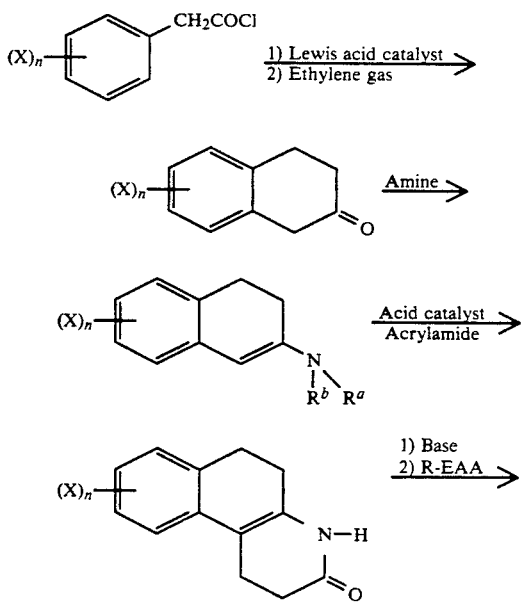

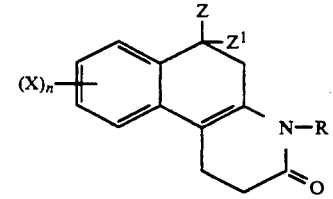

Where X, n, and R are as defined above for Formula I and R-EAA is an electrophilic alkylating agent, where EAA is a leaving group, and $R^a$ and $R^b$ are independently selected from hydrogen and $C_1$-$C_4$ alkyl, or may be taken together with the nitrogen atom to afford a 5-7 membered heterocyclic group which may also include an oxygen atom, provided that both $R^a$ and $R^b$ cannot simultaneously be hydrogen.

The hexahydrobenzo[f]quinolinones are prepared from an unsubstituted or appropriately ring-substituted phenacetyl chloride. The phenacetyl chloride is commercially available or is prepared by procedures well-known to those skilled in the art. Typically, suitably substituted phenylacetic acid is reacted with thionyl chloride, phosphorous trichloride, oxalyl chloride, or phosphorous pentachloride, preferably thionyl chloride, under conditions known to those skilled in the art, to afford the corresponding phenacetyl chloride.

By a Friedel-Crafts acylation reaction of the phenacetyl chloride with ethylene in the presence of a Lewis acid catalyst and in an inert or substantially inert solvent or mixture of solvents, acylation and subsequent ring closure are effected to afford a 2-tetralone. Suitable Lewis acid catalysts include $AlBr_3$, $AlCl_3$, $GaCl_3$, $FeCl_3$, $SbCl_5$, $ZrCl_4$, $SnCl_4$, $BCl_3$, $BF_3$, $SbCl_3$, and the like, preferably $AlCl_3$. Solvents useful in this reaction include carbon disulfide, methylene chloride, nitromethane, 1,2-dichloroethane, nitrobenzene, and the like, preferably methylene chloride. Activation of phenacetyl chloride with the Lewis acid is carried out at temperatures of from about −78° C. to about 25° C. Addition of ethylene is exothermic in nature and temperatures from about −78° C. to about 30° C. are maintained by standard cooling procedures.

The 2-tetralone reaction product is then aminated with a primary or secondary amine, preferably pyrrolidine, in an inert or substantially inert solvent or mixture of solvents to afford the corresponding enamine. In the case of a primary amine, this may be accomplished by the imine tautomer. The reaction is driven by the removal of water which may be accomplished at elevated temperatures of from about 80°-110° C. using a suitable solvent aeotrope or at about room temperature through the use of a suitable dehydrating agent such as molecular sieves or magnesium sulfate. Suitable solvents are aprotic organic solvents such as benzene, toluene, THF, $CH_2Cl_2$ and ethyl acetate.

The enamine reaction product is then reacted with acrylamide in the presence of an acid and in the presence or absence of an inert or substantially inert solvent or mixture of solvents to afford a hexahydro-2-(1H)-benzo[f]quinolinone. Acids useful in this reaction include strong organic or mineral acids, preferably p-toluene sulfonic acid (pTSA). Although the reaction can be carried out in a solvent, preferably no solvent is used. The reaction is carried out at temperatures of from about 90° C. to about 130° C.

The hexahydro-2(1H)-benzo[f]-quinolinone may be N-alkylated. The N-alkylation is carried out by reacting the hexahydrobenzo[f]quinolinone with a compound R-EAA where R-EAA is as defined above in the presence of a base, in an inert or substantially inert solvent or mixture of solvents. For this reaction, EAA is preferably iodo. The base is generally a metal hydride, metal amide or metal alkoxide, preferably sodium hydride. Generally, this reaction is carried out at temperatures of from about −30° C. to about solvent reflux.

Those compounds of the present invention where Z, $Z^1$, or both, are $C_1-C_4$ alkyl are prepared substantially according to the procedures in Scheme 1 except that during the Friedel-Crafts ring closure reaction of phenacetyl chloride, an appropriate alkene, is used, rather than the ethylene shown in Scheme 1. Examples of suitable alkenes for use in this reaction include propylene, 1-butene, 2-butene, isobutylene, 3,3-dimethyl-1-butene, 2-pentene, 4-methyl-2-pentene, 3-methyl-1-butene, 2-methyl-2-butene, 2,3-di-methyl-2-butene and the like.

Those compounds of Formula I where $R^1$ is $C_1-C_4$alkyl are prepared from the compounds afforded by Scheme 1 as shown in the following reaction Scheme 2:

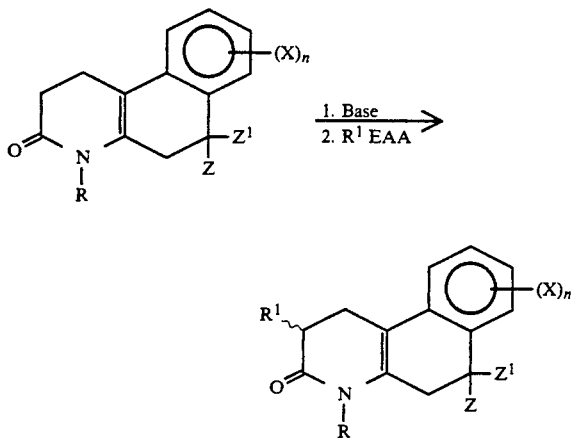

where X, n, R, and $R^1$-EAA are as defined above for Formula I and for Scheme 1.

The compound of Formula I is reacted with a base, such as a metal amide or metal alkoxide, preferably potassium hexamethyldisilazide in an inert or substantially inert solvent or mixture of solvents at a temperature of from about −78° C. to about 25° C. Alkylation is then effected by the addition of an appropriate electrophilic alkylating agent, preferably alkyl iodide, to afford the 2-($C_1-C_4$ alkyl) compounds of Formula I.

The 4(H) compounds of Formula I, are generally reacted with an amino protecting group, such as 2-(trimethylsilyl)ethyl prior to the 2-position alkylation. The amino protecting group reaction is carried out using standard procedures for such a reaction well known to those skilled in the art. After the 2-position alkylation, the 4-position nitrogen atom is deprotected, again using standard procedures for such a reaction as well known to those skilled in the art. The species of amino protecting group employed is not critical so long as the derivatized amino group is stable to the conditions of the subsequent reactions and can be removed at the appropriate point without disrupting the remainder of the molecule.

Alternatively, the 4(H) compounds of Formula I are reacted with two equivalents of base rather than one and then one equivalent of R-EAA in accordance with the Scheme 2 reaction and procedures described above for that reaction.

The optically active isomers of the racemates of the invention are also considered part of this invention. Such optically active isomers may be prepared from their respective optically active precursors by the procedures described above, or by resolving the racemic mixtures. This resolution can be carried out by derivatization with a chiral reagent followed, by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The pharmaceutically acceptable salts of the invention are typically formed by reacting a hexahydrobenzo[f]quinolinone of this invention which possesses suitable acidic or basic functionality with an equimolar or excess amount of acid or base. The reactants are generally combined in a mutual solvent such as diethyl ether or benzene, for acid addition salts, or water or alcohols for base addition salts, and the salt normally precipitates out of solution within about one hour to 10 days, and can be isolated by filtration.

In addition, some of the compounds of Formula I and their salts may form hydrates with water or solvates with common organic solvents. Such solvates and hydrates are included as compounds of this invention.

The following Examples further illustrate the compounds of the present invention and methods for their synthesis. The Examples are not intended to be limiting to the scope of the invention in any respect and should not be so construed.

EXAMPLE 1

Preparation of 8-bromo-1,2,3,4,5,6-hexahydrobenzo[f]quinolin-3-one.

A. 4-bromophenylacetyl chloride

To a 250 ml round bottom flask fitted with a magnetic stirrer was added 4-bromophenylacetic acid (100.0 g; 0.465 mol) and 100 ml of thionyl chloride (163.1 g; 1.37 mol). The resulting slurry was stirred at room temperature for 22.5 hrs. The excess thionyl chloride was evaporated under vacuum to afford 108.5 g of the subtitle compound as a brown liquid.

B. 6-bromo-2-tetralone

To a cold (−78° C.; dry ice/isopropanol bath) suspension of $AlCl_3$ (125 g; 0.94 mol) in 1.4 L $CH_2Cl_2$ was added the acid chloride afforded in Step A (108.5 g; 0.47 mol) dissolved in 400 ml of dry $CH_2Cl_2$ with stirring over one hour. The dry ice/isopropanol bath was removed and the solution was allowed to warm to −10° C. Ethylene was then bubbled into the flask with vigorous stirring. The reaction warmed exothermically to 20°

C. at which time the addition of ethylene was stopped. The mixture was stirred at room temperature for three hours, then it was cooled to 0° C. and ice added until no further exotherm was observed. The reaction mixture was diluted with 1 L of ice cold water and stirred until all solids dissolved. The resulting layers were separated and the organic layer washed twice with one liter portions of 1N HCl and then once with 1 L of saturated $Na_2CO_3$. The organic layer was dried over anhydrous $Na_2SO_4$ and concentrated under a vacuum to afford a pale yellow crystalline solid.

The 6-bromo-2-tetralone crystals were taken up in a minimum amount of ether. Hexane was cautiously added until the solution just started to turn cloudy and the mixture was refrigerated for four hours. The precipitated solid was collected by filtration and washed with cold hexanes to afford 75.6 g of the subtitle compound as pale yellow crystals (71% yield) melting point 71°-73° C.

C. 2-pyrrolidinyl-6-bromo-3,4-dihydronaphthalene

To a 250 ml round bottomed flask was added 5.00 g (22.21 mmol) of the 6-bromotetralone afforded above in Step B, 70 ml of dry toluene, and 3.1 g (3.7 ml) of pyrrolidine. The flask was equipped with a Dean-Stark trap, a condenser, a nitrogen inlet tube and a magnetic stirrer and the reaction mixture was refluxed for four hours. The solvent was evaporated under vacuum to afford 6.02 g (97.4%) of the subtitle compound as a brown crystalline material which was used without further purification.

D. 8-bromo-1,2,3,4,5,6-hexahydrobenzo[f]quinolin-3-one

The enamine (2.15 g; 7.73 mmol) from Step C, acrylamide (1.10 g; 15.46 mmol) and 100 mg of p-toluene sulfonic acid (pTSA) were mixed thoroughly in a mortar and pestle. The mixture was transferred to a 250 ml round bottomed flask equipped with a magnetic stirrer and nitrogen inlet. The mixture was stirred and heated to 89° C. in a mineral oil bath at which point it turned black and melted. The temperature was held constant at 89° C. for 1.5 hours. The temperature was then increased to 130° C. and held there for 0.5 hours. The oil bath was removed and 60 ml of water was cautiously added. The resulting murky gray material was mixed thoroughly with a spatula and 80 ml of water was added to aid in filtration. Brown crystals (1.02 grams) were afforded by the filtration. The crystals were taken up in $CHCl_3$ and activated carbon was added. This mixture was stirred for 15 minutes, filtered, and evaporated under vacuum. The residue was taken up in a minimum amount of ethyl acetate with the help of a steam bath, and transferred to an Erlenmeyer flask, equipped with a magnetic stirring bar and sub-merged in a dry ice/acetone bath with stirring to afford the subtitle compound as a white crystalline solid (melting point 215°-217° C. decomp.). Yield: 1.12 g.

| | Elemental Analysis: | | |
|---|---|---|---|
| | C | H | N |
| Calculated: | 56.14 | 4.35 | 5.04 |
| Found: | 56.40 | 4.58 | 5.07 |

EXAMPLE 2

8-bromo-4-methyl-1,2,3,4,5,6-hexahydrobenzo[f]quinolin-3-one

By substantially following the procedures described above in Example 1 5.17 g of 8-bromo-1,2,3,4,5,6-hexahydrobenzo[f]quinolin-3-one was obtained. The hexahydrobenzoquinolinone (5.17 g; 19.6 mmol) was dissolved in 60 ml of dry diethyl ether in a 250 ml round bottomed flask. To the solution was added 1.2 g of sodium hydride (60% dispersion in mineral oil). The flask was fitted to a reflux condenser with a stirring bar and the mixture refluxed for 2 hours. The mixture was then cooled to room temperature and 7.35 ml of methyl iodide was added. After addition, the reaction mixture was refluxed for an additional 3 hours. After cooling, the reaction mixture was quenched by the cautious addition of 5 ml of water. The mixture was then concentrated under vacuum affording a pale solid which was taken up in a ethyl acetate/water mixture and the resulting layers separated. The organic layer was washed twice with water and once with brine and then dried over $MgSO_4$ and concentrated under vacuum to afford 5.22 g of a yellow crystalline solid. The solid was recrystallized from acetone to afford 3.55 g (62%) of the subtitle compound as a pale yellow solid. Melting point 126°-128° C.

| | Elemental Analysis: | | |
|---|---|---|---|
| | C | H | N |
| Calculated: | 57.55 | 4.83 | 4.79 |
| Found: | 57.40 | 4.92 | 4.74 |

EXAMPLE 3

Preparation of 8,9-dichloro-1,2,3,4,5,6-hexahydrobenzo[f]quinolin-3-one

The title compound was prepared employing 3,4-dichlorophenylacetic acid as the starting material according to the procedures described above in Example 1 to afford 4.34 g of the title compound. Melting point 251°-253° C. decomp.

| | Elemental Analysis: | | |
|---|---|---|---|
| | C | H | N |
| Calculated: | 58.23 | 4.14 | 5.22 |
| Found: | 58.36 | 4.37 | 5.36 |

EXAMPLE 4

Preparation of 8-chloro-4-methyl-1,2,3,4,5,6-hexahydrobenzo[f]quinolin-3-one

The title compound was prepared according to the procedures described in Examples 1 and 2 using p-chlorophenylacetic acid as the starting material to afford the title compound Yield: 62.5%. Melting point 140°-141° C.

| | Elemental Analysis: | | |
|---|---|---|---|
| | C | H | N |
| Calculated: | 67.88 | 5.70 | 5.65 |

| -continued | | | |
|---|---|---|---|
| | Elemental Analysis: | | |
| | C | H | N |
| Found: | 67.64 | 5.70 | 5.62 |

EXAMPLE 5

Preparation of 4,8-dimethyl-1,2,3,4,5,6-hexahydrobenzo[f]quinolin-3-one

The title compound was prepared according to the procedures described in Examples 1 and 2 using p-tolylacetic acid as the starting material. Yield: 55%. Melting point 122° C.

| | Elemental Analysis: | | |
|---|---|---|---|
| | C | H | N |
| Calculated: | 79.26 | 7.54 | 6.16 |
| Found: | 79.03 | 7.48 | 6.09 |

EXAMPLE 6

Preparation of 8-fluoro-4-methyl-1,2,3,4,5,6-hexahydrobenzo[f]quinolin-3-one

The title compound was prepared according to the procedures described in Examples 1 and 2 using p-fluorophenylacetic acid as the starting material. Melting point 108° C.

| | Elemental Analysis: | | |
|---|---|---|---|
| | C | H | N |
| Calculated: | 72.71 | 6.10 | 6.06 |
| Found: | 72.93 | 6.21 | 6.08 |

EXAMPLE 7

Preparation of 4-methyl-1,2,3,4,5,6,-hexahydrobenzo[f]quinolin-3-one

Yield: 40.5 %. Melting point 100° C.
The title compound was prepared according to the procedures described in Examples 1 and 2 using phenylacetic acid as the starting material.

| | Elemental Analysis: | | |
|---|---|---|---|
| | C | H | N |
| Calculated: | 78.84 | 7.09 | 6.57 |
| Found: | 79.04 | 7.17 | 6.58 |

EXAMPLE 8

Preparation of 1,2,3,4,5,6-hexahydrobenzo[f]quinolin-3-one

The title compound, 1,2,3,4,5,6-hexahydrobenzo[f]quinolin-3-one was prepared according to the procedures described in Example 1 using phenylacetic acid as the starting material. Melting point 176°–177° C.

| | Elemental Analysis: | | |
|---|---|---|---|
| | C | H | N |
| Calculated: | 78.36 | 6.58 | 7.03 |

| -continued | | | |
|---|---|---|---|
| | Elemental Analysis: | | |
| | C | H | N |
| Found: | 78.29 | 6.71 | 7.04 |

EXAMPLE 9

Preparation of 8-fluoro-1,2,3,4,5,6-hexahydrobenzo[f]quinolin-3-one

The title compound was prepared according to the procedures described in Example 1 using p-fluorophenylacetic acid as the starting material. Yield: 31.8%. Melting point 222°–223° C.

| | Elemental Analysis: | | |
|---|---|---|---|
| | C | H | N |
| Calculated: | 71.87 | 5.57 | 6.45 |
| Found: | 72.10 | 5.54 | 6.30 |

EXAMPLE 10

Preparation of 8-chloro-1,2,3,4,5,6-hexahydrobenzo[f]quinolin-3-one

The title compound was prepared according to the procedures described in Example 1 using p-chlorophenylacetic acid as the starting material. Yield: 35%. Melting point 229°–230° C.

| | Elemental Analysis: | | |
|---|---|---|---|
| | C | H | N |
| Calculated: | 66.81 | 5.18 | 5.99 |
| Found: | 66.57 | 5.24 | 5.92 |

EXAMPLE 11

Preparation of 8-methoxy-1,2,3,4,5,6-hexahydrobenzo[f]quinolin-3-one

The title compound was prepared according to the procedures described in Example 1 using p-methoxyphenylacetic acid as the starting method. Yield: 40%. Melting point 203°–204° C.

| | Elemental Analysis: | | |
|---|---|---|---|
| | C | H | N |
| Calculated: | 73.34 | 6.59 | 6.11 |
| Found: | 73.20 | 6.45 | 5.91 |

EXAMPLE 12

Preparation of 8-methoxy-4-methyl-1,2,3,4,5,6-hexahydrobenzo[f]quinolin-3-one

The title compound is prepared according to the procedures described in Example 1 using p-methoxyphenylacetic acid as the starting material.

EXAMPLE 13

Preparation of 8-methyl-1,2,3,4,5,6-hexahydrobenzo[f]quinoline-3-one

The title compound was prepared according to the procedures described in Example 1 using p-tolylacetic acid as the starting material. Yield: 30%. Melting point 204°-205° C.

Elemental Analysis:

|  | C | H | N |
|---|---|---|---|
| Calculated: | 78.84 | 7.09 | 6.57 |
| Found: | 78.63 | 7.24 | 6.44 |

EXAMPLE 14

Preparation of 8-bromo-6,6-dimethyl-1,2,3,4,5,6-hexahydrobenzo[f]quinolin-3-one 4,4-dimethyl-6-bromo-2-tetralone was prepared according to the procedures described in Example 1, Steps A and B with the exception that isobutylene was used in Step B rather than ethylene. The title compound was prepared from this tetralone according to the procedures described in Example 1, Steps C and D. Recrystallization from DMF/H₂O afforded 1.93 g (23% yield) of the title compound. Melting point 263°-265° C.

Elemental Analysis:

|  | C | H | N |
|---|---|---|---|
| Calculated: | 58.84 | 5.27 | 4.57 |
| Found: | 59.10 | 5.52 | 4.75 |

EXAMPLE 15

Preparation of 8-t-butyl-1,2,3,4,5,6-hexahydrobenzo[f]quinoline-3-one

A. 6-t-butyl-2-naphthol

A 2 L round bottomed flask was charged with freshly fused zinc chloride (45.0 g.); β-naphthol (150.0 g; 1.04 mol) and hexanes (450 ml). The mixture was stirred vigorously while adding t-butyl chloride (150.0 g; 1.62 mol) dropwise over 30 min. When the reaction mixture was gradually heated to reflux, a solution was not obtained. The reaction mixture was cooled to room temperature and 100 ml of $CH_2Cl_2$ was added. The reaction mixture was refluxed overnight, cooled and concentrated under vacuum to afford a white solid. The solid was refluxed with 1800 ml of 10% NaOH, filtered, and allowed to cool. The white sodium salt which precipitated was collected by filtration. The solid collected by filtration was stirred with excess 5.0M HCl and the resulting phenol was collected by filtration and washed with 2 L of water. Recrystallization from heptane afforded 30.67 g of the subtitle compound as a white solid.

B. 6-t-butyl-2-methoxynaphthalene

To a 2 L round bottomed flask was added 6-t-butyl-2-naphthol (30.67 g; 0.153 mmol) and 550 ml of 15% KOH in water. The solution was stirred while adding dimethyl sulfate (6.0 equiv.) dropwise over 30 min. After the addition was complete, the mixture was allowed to stir for 2 hrs. The solids were collected on a filter and washed with water to afford 28.97 g (88% yield) of the subtitle compound.

C. 6-t-butyl-2-tetralone

To a stirred solution of 6-t-butyl-2-methoxynaphthalene (28.97 g; 0.135 mmol) in 350 ml of anhydrous ethanol was added sodium spheres (36 g; 11.5 equiv.) over 2 hrs. at a rate so as to maintain a gentle reflex. The viscous reaction mixture was stirred until all of the sodium had dissolved. The mixture was cooled and 140 ml of water was cautiously added. Concentrated HCl (275 ml) was added and the reaction mixture was refluxed for 30 minutes. After cooling, the reaction mixture was filtered and the aqueous layer was extracted 3 times with toluene. Evaporation of the volatiles under vacuum afforded 28.1 g of a red viscous oil. The oil was taken up in 300 ml of diethyl ether and stirred with 50 ml of saturated aqueous $NaHSO_3$ overnight. The resulting white precipitate was collected by filtration and washed several times with hexanes. This material was partially dissolved in 500 ml of $H_2O$ and 200 ml of diethyl ether was added. The mixture was vigorously stirred and 300 ml of saturated aqueous $Na_2CO_3$ added. The mixture was stirred for one hour, the layers were separated, and the aqueous layer was extracted 3 times with diethyl ether. The combined organic layers were combined, washed with brine, dried over $MgSO_4$ and concentrated under vacuum to afford 5.74 g of the subtitle compound as an orange oil which crystallized slowly on standing.

D. 6-t-butyl-2-pyrrolidinyl-3,4-dihydronaphthalene

To a stirred solution of 6-t-butyl-2-tetralone (5.74 g; 28.37 mmol) in 100 ml of toluene was added 1.5 equiv. of pyrrolidine (3.56 ml; 42.56 mmol). A 100 mg portion of p-toluenesulfonic acid was added and the mixture was refluxed. The water eliminated during the reaction was collected by a Dean Stark trap. After a reflux time of 3.5 hours, concentration of the volatiles under vacuum afforded 7.31 g of the subtitle compound as a purple solid.

E. 8-t-butyl-1,2,3,4,5,6-hexahydrobenzo[f]quinolin-3-one

To 6-t-butyl-2-pyrrolidinyl-3,4-dihydronaphthalene (7.25 g; 28.37 mmol) was added 3.0 equiv. of acrylamide (6.05 g; 85.11 mmol). The reaction mixture was stirred at 89° C. overnight. The temperature was then increased to 130° C. and held there for 20 minutes. Water (100 ml) was cautiously added and the reaction mixture was cooled to room temperature. The resulting solid was triturated with water and collected on a filter to afford a brown solid. The soid was recrystallized twice from dimethyl formamide (DMF)/H₂O to afford 4.56 g (63% yield) of the subtitle compound. Melting point 265°-268° C.

Elemental Analysis:

|  | C | H | N |
|---|---|---|---|
| Calculated: | 79.96 | 8.29 | 5.47 |
| Found: | 80.26 | 8.25 | 5.08 |

EXAMPLE 16

Preparation of 10-bromo-1,2,3,4,5,6-hexahydrobenzo[f]quinolin-3-one

The title compound was prepared according to the procedures described in Example 1 using 8-bromotetralone as the starting material. Yield: 20 mg. Melting point 189°-189.5° C.

Elemental Analysis:

|  | C | H | N |
|---|---|---|---|
| Calculated: | 56.14 | 4.35 | 5.04 |
| Found: | 56.40 | 4.25 | 5.02 |

EXAMPLE 17

Preparation of
10-chloro-1,2,3,4,5,6-hexahydrobenzo[f]quinolin-3-one

The title compound, was prepared according to the procedures described in Example 1, using 8-chlorotetralone as the starting material. Yield: 750 mg. Melting point 184.5° C.

| | Elemental Analysis: | | |
|---|---|---|---|
| | C | H | N |
| Calculated: | 66.81 | 5.18 | 5.99 |
| Found: | 66.56 | 5.24 | 6.00 |

EXAMPLE 18

Preparation of
7-fluoro-1,2,3,4,5,6-hexahydrobenzo[f]quinolin-3-one

The title compound was prepared according to the procedures described in Example 1 using 3-fluoro phenylacetic acid as the starting material. Yield: 265 mg; (20%) Melting point 233°–234° C.

| | Elemental Analysis: | | |
|---|---|---|---|
| | C | H | N |
| Calculated: | 71.87 | 5.57 | 6.45 |
| Found: | 72.09 | 5.69 | 6.33 |

EXAMPLE 19

Preparation of
7-fluoro-4-methyl-1,2,3,4,5,6-hexahydrobenzo[f]quinolin-3-one

The title compound was prepared according to the procedures described in Examples 1 and 2 using 3-fluorophenylacetic acid as the starting material. Melting point 137°–138° C. Yield: 98 mg; 62.8%.

| | Elemental Analysis: | | |
|---|---|---|---|
| | C | H | N |
| Calculated: | 72.71 | 6.10 | 6.06 |
| Found: | 72.42 | 6.26 | 5.94 |

EXAMPLE 20

Preparation of
10-fluoro-1,2,3,4,5,6-hexahydrobenzo[f]quinolin-3-one

The title compound was prepared according to the procedures described in Example 1 using 2-fluorophenylacetic acid as the starting material. Yield: 180 mg; (8%). Melting point 199° C.

| | Elemental Analysis: | | |
|---|---|---|---|
| | C | H | N |
| Calculated: | 71.87 | 5.57 | 6.45 |
| Found: | 71.84 | 5.39 | 6.35 |

EXAMPLE 21

Preparation of
9-fluoro-4-methyl-1,2,3,4,5,6-hexahydrobenzo[f]quinolin-3-one

The title compound was prepared according to the procedures described in Examples 1 and 2 using 3-fluorophenylacetic acid as the starting material. Yield: 370 mg; 69.5%. Melting point 122° C.

| | Elemental Analysis: | | |
|---|---|---|---|
| | C | H | N |
| Calculated: | 72.71 | 6.10 | 6.06 |
| Found: | 72.90 | 6.28 | 6.36 |

EXAMPLE 22

Preparation of
10-fluoro-4-methyl-1,2,3,4,5,6-hexahydrobenzo[f]quinolin-3-one

The title compound was prepared according to the procedures described in Examples 1 and 2 using 2-fluoro phenylactic acid as the starting material. Yield: 195 mg; (36.7%). Melting point 75°–76° C.

| | Elemental Analysis: | | |
|---|---|---|---|
| | C | H | N |
| Calculated: | 72.71 | 6.10 | 6.06 |
| Found: | 72.63 | 6.31 | 6.11 |

EXAMPLE 23

Preparation of
8-fluoro-4-benzyl-1,2,3,4,5,6-hexahydrobenzo[f]quinolin-3-one

The title compound was prepared according to the procedures described in Examples 1 and 2 using 4-fluoro phenylacetic acid as the starting material and N-alkylated using benzyl chloride. Yield: 370 mg; (41%). Melting point 101°–102° C.

| | Elemental Analysis: | | |
|---|---|---|---|
| | C | H | N |
| Calculated: | 78.15 | 5.90 | 4.56 |
| Found: | 78.38 | 5.83 | 4.59 |

EXAMPLE 24

Preparation of
8-fluoro-4-ethyl-1,2,3,4,5,6-hexahydrobenzo[f]quinolin-3-one

The title compound was prepared according to the procedures described in Examples 1 and 2 using 4-fluoro phenylacetic acid as the starting material. Yield: 66 mg; (11%). Melting point 72° C.

| | Elemental Analysis: | | |
|---|---|---|---|
| | C | H | N |
| Calculated: | 73.45 | 6.57 | 5.71 |
| Found: | 73.53 | 6.29 | 5.64 |

EXAMPLE 25

Preparation of
8-fluoro-4-n-butyl-1,2,3,4,5,6-hexahydrobenzo[f]quinolin-3-one

The title compound was prepared according to the procedures described in Examples 1 and 2 using 4-fluoro phenylacetic acid as the starting material. Melting point: oil.

|  | Elemental Analysis: | | |
| --- | --- | --- | --- |
|  | C | H | N |
| Calculated: | 74.70 | 7.37 | 5.12 |
| Found: | 74.49 | 7.27 | 5.09 |

EXAMPLE 26

Preparation of
9-methoxy-1,2,3,4,5,6-hexahydrobenzo[f]quinolin-3-one

The title compound was prepared according to the procedures described in Example 1 using 7-methoxy-2-tetralone as the starting material. Yield: 4.5 g; (33%). Melting point 227°–228° C.

|  | Elemental Analysis: | | |
| --- | --- | --- | --- |
|  | C | H | N |
| Calculated: | 73.34 | 6.59 | 6.11 |
| Found: | 73.59 | 6.62 | 6.14 |

EXAMPLE 27

Preparation of
10-methoxy-1,2,3,4,5,6-hexahydrobenzo[f]quinolin-3-one

The title compound was prepared according to the procedures described in Example 1 using 8-methoxy-2-tetralone as the starting material. Yield: 110 mg; (25%). Melting point 190°–190.5° C.

|  | Elemental Analysis: | | |
| --- | --- | --- | --- |
|  | C | H | N |
| Calculated: | 73.34 | 6.59 | 6.11 |
| Found: | 73.38 | 6.33 | 5.96 |

EXAMPLE 28

Preparation of
8,9-dimethoxy-1,2,3,4,5,6-hexahydrobenzo[f]quinolin-3-one

The title compound was prepared according to the procedures described in Example 1 using 6,7-dimethoxy-2-tetralone as the starting material. Yield: 170 mg; (50%). Melting point 270°–271° C.

|  | Elemental Analysis: | | |
| --- | --- | --- | --- |
|  | C | H | N |
| Calculated: | 69.48 | 6.61 | 5.40 |
| Found: | 69.62 | 6.88 | 5.66 |

EXAMPLE 29

Preparation of
10-methyl-1,2,3,4,5,6-hexahydrobenzo[f]quinolin-3-one

The title compound was prepared according to the procedures described in Example 1 using 8-methyl-2-tetralone as the starting material. Yield: 280 mg; (23%). Melting point 168°–169° C.

|  | Elemental Analysis: | | |
| --- | --- | --- | --- |
|  | C | H | N |
| Calculated: | 78.84 | 7.09 | 6.57 |
| Found: | 79.03 | 7.09 | 6.49 |

By substantially following the procedures described above one skilled in the art can prepare the compounds of Formula I.

As noted above, the compounds of the present invention are useful for inhibiting the conversion of testosterone to 5α-dihydrotestosterone (DHT). Therefore, another embodiment of the present invention is a method for inhibiting 5α-reductase by administering to a mammal in need of 5α-reductase inhibition a 5α-reductase inhibiting dose (effective amount) of a compound according to Formula I or a pharmaceutically acceptable salt thereof.

The term "effective amount" as used herein, means an amount of a compound of the present invention which is capable of inhibiting the conversion of testosterone to 5α-dihydrotestosterone which is catalyzed by the enzyme 5α-reductase and particularly, inhibiting 5α-reductase. The 5α-reductase inhibition contemplated by the present method includes both medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of the active compound of this invention. Preferred daily doses generally will be from about 0.05 to about 20 mg/kg and ideally from about 0.1 to about 10 mg/kg.

A variety of physiologic functions have been associated with 5α-dihydrotestosterone. As such, the compounds of this invention are believed to have the ability to treat in mammals a variety of disorders associated with 5α-dihydrotestosterone including benign prostatic hyperplasia (or hypertrophy), male pattern baldness, acne vulgaris, hirsutism and prostatic cancer. Therefore, the present invention also provides methods of treating the above disorders at the rates set forth above for inhibiting the 5α-reductase catalyzed conversion of testosterone to 5α-dihydrotestosterone.

The compounds can be administered by a variety of routes including oral, rectal, transdermal, subcutaneous, intravenous, intramuscular, intranasal, and topical for male pattern baldness, acne vulgaris and hirsutism. The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor, preferably in unit dosage form to afford a daily dose of from about 0.01 mg/kg to about 50 mg/kg of body weight of said compound of Formula I.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules suppositories, sterile injectable solutions, sterile packaged powders, and the like. Typical formulations designed for topical administration include ointments, creams, gels and lotions containing, for example, up to 10% by weight of the active ingredient.

The following formulation examples are illustrative only and are not intended to limit the scope of the invention in any way. "Active ingredient," of course, means a compound according to Formula I or a pharmaceutically acceptable salt thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighting 665 mg

FORMULATION 3

An aerosol solution is prepared containing the following components:

|  | Weight |
| --- | --- |
| Active ingredient | 0.25 |
| Ethanol | 25.75 |
| Propellant 22 | 70.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighting 150 mg.

FORMULATION 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient customarily is added in an amount to achieve the desired concentration.

Gels comprise a base selected from an oleaginous base, water, or an emulsion-suspension base, such as described above. To the base is added a gelling agent which forms a matrix in the base, increasing its viscosity. Examples of gelling agents are hydroxypropyl cellulose, acrylic acid polymers, and the like. Customarily, the active ingredient is added to the formulation at the desired concentration at a point preceding addition of the gelling agent.

The amount of active ingredient incorporated into the formulation of this invention is not critical; the concentration should only be in a range sufficient to permit ready application of the formulation to the area of administration in an amount which will deliver the desired amount of active ingredient.

The following experiments were carried out to demonstrate the ability of the compounds of the present invention to inhibit 5a-reductase.

Cell Culture: 5α-Reductase activity was measured using Hs68 human genital skin fibroblasts which were originally purchased from the American Type Culture Collection (Rockville, Md.). The cells were grown in Dulbecco's Modified Eagle's Medium (DMEM) plus 10% stripped fetal bovine serum which was supplemented with amphotericin B (0.25 µg/ml) and gentamicin (25.0 µg/ml) (GIBCO, Grand Island, N.Y.). The serum was stripped of endogenous steroids by incubation with dextran-coated charcoal prior to its addition to the media. The cells were maintained at 37° C. in an atmosphere of 95% air, 5% $CO_2$ and were passaged every 7–10 days by exposure to a trypsin-EDTA solution (0.025% trypsin, 0.265 mM EDTA). Prior to the assay the Hs68 cells were harvested and plated in Falcon 6-well plates (Becton Dickinson Labware, Lincoln Park, N.J.) at a density of $6 \times 10^4$ cells per well. The cells were allowed to grow for 4–5 days or until they reached approximately 80% confluence.

Assay Method I: The substrate was prepared by dissolving unlabeled testosterone (Sigma Chemical Co., St. Louis, Mo.) in absolute ethanol followed by the addition of [7-$^3$H (N)]-testosterone (23.3 Ci/mmole, New England Nuclear, Boston, Mass.). The steroid solution was taken to dryness under a stream of nitrogen and then reconstituted in media.

Assay Method II: The substrate used for this method was [$^{14}$C]-testosterone (50 mCi/mmol) (New England Nuclear, Boston, Mass.). An aliquot of the substrate was taken to dryness under a stream of nitrogen. After the addition of 30 µl of ethanol, the testosterone was brought up in an appropriate volume of media.

Sample Preparation: The test compounds were dissolved in absolute ethanol in order to achieve the desired concentration. Subsequent dilutions of the test compounds with media were performed by the Biomek 1000 Automated Laboratory Workstation (Beckman Instruments, Palo Alto, Calif.). The existing media in the sample wells was aspirated and replaced with fresh media. Test compound was then added to the wells followed by the addition of 0.5 ml of the substrate. The volume of the incubation mixture was maintained at 2.0 ml. The final substrate concentration was 12 µM. The concentration of the test compounds ranged from 0.001–15 µM. An additional three wells (background) containing media and substrate but no cells were also included to account for the non-enzymatic metabolism of the substrate. The plates were returned to the incubator and incubated for four hours.

At the end of the incubation the media was collected and transferred to an extraction tube containing 5 ml of tolueneethanol (9:1), to which has been added 40–250 µg each of unlabeled carrier steroids (estriol, estradiol, estrone, 5α-androstan-3α,17β-diol, 5α-androstan-3β,17β-diol, 4-androstene-3,17-dione, 5α-androstan-3,17-dione, testosterone, and 5α-dihydrotestosterone) (Steraloids, Inc. Wilton, N.H.). In the case of Assay Method I the extraction tube also contained 1,000 and 10,000 dpm of [4-$^{14}$C]-dihydrotesterone (50–60 mCi/m- mol) and [4-$^{14}$C]-testosterone (50 mCi/mmol) (New England Nuclear, Boston, Mass.), respectively. The [$^{14}$C]-steroids were included as recovery standards to quantify procedural losses. A small amount of NaCl was also added to the extraction tubes to prevent foaming. The samples were vortexed for approximately 30 seconds and then centrifuged for 10 minutes at 500×g. The organic phase was collected and the samples taken to dryness, redissolved in dichloromethane-methanol (9:1) and were analyzed by thin layer chromatography using one of the methods described below.

Chromatography Method I (two-dimensional): The extracted samples were applied to silica gel 60F$_{254}$, 0.25 mm thick, thin layer chromatography plates (EM Science, Cincinnati, Ohio. The plates were developed in the first dimension with a solvent system containing dichloromethane-ethyl acetate-methanol-acetic acid (160:38:1.5:0.5, Mallinckrodt Inc., Paris, Ky.). The plates were removed from the tanks and allowed to dry before they were developed in the second dimension in a solvent system containing dichloromethane-methanol-ammonium hydroxide (180:19:1, Mallinckrodt Inc., Paris, Ky.).

Chromatography Method II (one-dimensional): The extracted samples were applied to silica gel 60F, 0.25 mm thick, thin layer chromatography plates (EM Science, Cincinnati, Ohio). The plates were developed in a solvent system containing either cyclohexane-ethyl acetate (1:1, Mallinckrodt Inc., Paris, Ky.) or chloroform-ethyl acetate (3:1, Mallinckrodt Inc., Paris, Ky.). Both of these solvent systems gave adequate separation and enabled a greater throughout when compared to the two-dimensional system described above.

The plates were initially viewed under 254 mm UV light and the visible spots marked. The plates were then sprayed with primulin (Aldrich Chemical Co., Milwaukee, Wis.) (0.001% in acetone-water (4:1)) according to the method of Wright, R.S., "A reagent for the non-destructive localization of steroids and some other lipophilic materials on silica gel thin-layer chromatograms," *J. Chromatogr.*, 59; 220-221 (1971) which allowed the identification of additional steriods under 365 mm UV light. Samples derived using Assay Method II were analyzed directly using the Ambis Radioanalytic Imaging System (Ambis Systems, Inc., San Diego, CA). In the case of samples run using Assay Method I, the spots were scraped from the plate using a glass wool plugged Pasteur pipet attached to a vacuum line. The steroids were eluted directly into scintillation vials by the addition of 0.2 ml of dichloromethane followed by two washes of 2.0 ml of methanol. The organic solvent was evaporated, and 10.0 ml of scintillation fluid (Ready Organic, Beckman Instruments, Inc. Fullerton, CA) were added. Samples were analyzed by liquid scintillation spectrometry.

Following removal of the media for extraction, the cells were washed with phosphate buffered saline (PBS, pH 7.4), and then harvested by exposure to a trypsin-EDTA solution (0.025% trypsin, 0.265 mM EDTA). The cells were collected and centrifuged at 1400× g for 5 minutes. The supernatant was decanted and the cells were resuspended in PBS. An aliquot of the cell suspension was counted in a Coulter Counter Model ZM (Coulter Electronics, Ltd., Luton Beds, England). The remaining cells were sonicated, and the protein was determined according to the method of Bradford, M.M., "A rapid and sensitive method for protein quantitation of microgram quantities of protein utilizing the principle of protein-dye binding," *Anal. Biochem.*, 72; 248-254 (1976). Corrections were made for procedural losses, and the data was expressed as percent inhibition based on either steroid concentration in terms of picomoles per mg/protein or picomoles/10$^5$ cells.

Evaluation results are given in Table I. Percent inhibition is used on a scale of 0-100 percent where 0 equals no activity and 100 equals total inhibition.

TABLE I

| Example | Concentration μM | % Inhibition |
|---|---|---|
| 1 | 0.316 | 73 |
| 2 | 10.0 | 98 |
| 3 | 0.316 | 85 |
| 4 | 10.0 | 91 |
| 5 | 10.0 | 100 |
| 6 | 10.0 | 81 |
| 7 | 1.00 | 48 |
| 8 | 10.0 | 63 |
| 9 | 10.0 | 76 |
| 10 | 1.00 | 81 |
| 11 | 1.00 | 20 |
| 13 | 10.0 | 100 |
| 14 | 0.316 | 30 |
| 15 | 3.16 | 30 |
| 16 | 1.0 | 14 |
| 17 | 1.0 | 0.3 |
| 18 | 1.0 | 36 |
| 19 | 1.0 | 61 |
| 20 | 1.0 | 22 |
| 21 | 1.0 | 60 |
| 22 | 1.0 | 35 |
| 23 | 1.0 | 37 |
| 24 | 1.0 | 31 |
| 25 | 10.0 | 56 |
| 26 | 1.0 | 12 |
| 27 | 1.0 | 0 |
| 28 | 1.0 | 33 |
| 29 | 1.0 | 41 |

It should be understood that the instant specification and examples are set forth by way of illustration and not limitation, and that various modifications and changes may be made without departing from the spirit and scope of the present invention as defined by the appended claims.

We claim:

1. A compound having the Formula

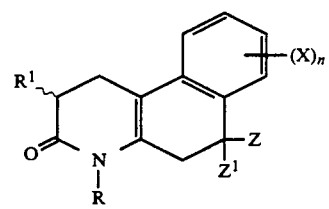

where:
R is hydrogen, C$_1$-C$_4$ alkyl, unsubstituted or substituted phen(C$_1$-C$_4$)alkyl where the substituent is on the phenyl ring and is selected from halogen, C$_1$-C$_4$ alkyl, C$_1$-C$_4$ alkoxy, amino, C$_1$-C$_4$ alkylamino, or C$_1$-C$_4$ dialkylamino;

Z and Z$^1$ are independently selected from hydrogen and C$_1$-C$_4$ alkyl;

R1 is hydrogen or C$_1$-C$_4$ alkyl;

n is 1 or 2;

X is halogen, NO$_2$, cyano, CF$_3$, C$_1$-C$_6$ alkyl, C$_1$-C$_6$ alkoxy, carboxy, C$_1$-C$_6$ alkoxycarbonyl, amino, C$_1$-C$_4$ alkylamino, C$_1$-C$_4$ dialkylamino, amido, $C_1-C_4$ alkylamido, $C_1-C_4$ dialkylamido, mercapto, $C_1-C_6$ alkylthio, $C_1-C_6$ alkylsulfinyl, $C_1-C_6$ alkylsulfonyl, or a group —A—$R^2$ where A is $C_1-C_6$ alkylene $C_2-C_6$ alkenylene or $C_2-C_6$ alkynylene; and $R^2$ is halogen, hydroxy, $CF_3$, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl, and pharmaceutically acceptable salts thereof; provided that:

(a) when R is hydrogen, X is not halo or methoxy;
(b) when R is methyl, ethyl or benzyl, X is not methoxy; and
(c) when R is methyl, $R^1$ is not methyl.

2. A compound according to claim 1 where:
R is hydrogen or $C_1-C_4$ alkyl;
Z and $Z^1$ are independently hydrogen or methyl;
$R^1$ is hydrogen or methyl;
n is 1 or 2;
X is halogen, $CF_3$, $C_1-C_6$ alkyl, $C_1-C_4$ alkoxy or —A—$R^2$ where A is $C_1-C_4$ alkylene and $R_2$ is $C_1-C_4$ alkoxycarbonyl; and pharmaceutically acceptable salts thereof; provided that:

(a) when R is hydrogen, X is not hydrogen, halo or methoxy;
(b) when R is methyl or ethyl, X is not methoxy; and
(c) when R is methyl, $R^1$ is not methyl.

3. A compound according to claim 2 where
R is hydrogen or methyl;
Z and $Z_1$ are hydrogen or methyl;
$R_1$ is hydrogen or methyl;
n is 1 or 2;
X is halogen, $CF_3$, or $C_1-C_4$ alkyl; and pharmaceutically acceptable salts thereof; provided that:

(a) when R is hydrogen, X is not halogen;
(b) when R is methyl, $R^1$ is not methyl.

4. A compound according to claim 3 which is 8-bromo-4-methyl-1,2,3,4,5,6-hexahydrobenzo[f]quinolin-3-one or a pharmaceutically acceptable salt thereof.

5. A compound according to claim 3 which is 4,8-dimethyl-1,2,3,4,5,6-hexahydrobenzo[f]quinolin-3-one or a pharmaceutically acceptable salt thereof.

6. A compound according to claim 3 which is 8-methyl-1,2,3,4,5,6-hexahydrobenzo[f]quinolin-3-one or a pharmaceutically acceptable salt thereof.

7. A pharmaceutical formulation which comprises, in association with a pharamaceutically acceptable carrier, diluent, or excipient, a compound of the Formula

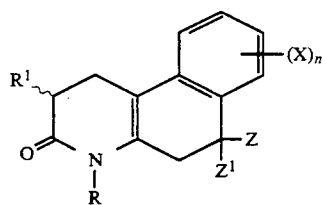

I where:
R is hydrogen, $C_1-C_4$ alkyl, unsubstituted or substituted phen($C_1-C_4$)alkyl;
Z and $Z^1$ are independently selected from hydrogen and $C_1-C_4$ alkyl;
$R^1$ is hydrogen or methyl;
n is 1 or 2;

X is hydrogen, halogen, $NO_2$, cyano, $CF_3$, $C_1-C_6$ alkyl, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, mercapto, $C_1-C_6$ alkylthio, $C_1-C_6$ alkylsulfinyl, $C_1-C_6$ alkylsulfonyl, or a group —A—$R^2$ where A is $C_1-C_6$ alkylene $C_2-C_6$ alkenylene or $C_2-C_6$ alkynylene; and $R^2$ is halogen, hydroxy, $CF_3$, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl, and pharmaceutically acceptable salts thereof.

8. A formulation according to claim 7 where:
R is hydrogen or $C_1-C_4$ alkyl;
Z and $Z^1$ are independently hydrogen or methyl;
$R^1$ is hydrogen or methyl;
n is 1 or 2;
X is halogen, $CF_3$, $C_1-C_6$ alkyl, $C_1-C_4$ alkoxy or —A—$R^2$ where A is $C_1-C_4$ alkylene and $R^2$ is $C_1-C_4$ alkoxycarbonyl; and pharmaceutically acceptable salts thereof.

9. A formulation according to claim 8 where:
R is hydrogen or methyl;
Z and $Z^1$ are both hydrogen or methyl;
$R^1$ is hydrogen or methyl;
n is 1 or 2;
X is halogen, $CF_3$, or $C_1'-C_4$ alkyl; and pharmaceutically acceptable salts thereof.

10. A formulation according to claim 9 wherein said compound is 8-bromo-4-methyl-1,2,3,4,5,6-hexahydrobenzo-[f]quinolin-3-one or a pharmaceutically acceptable salt thereof.

11. A formulation according to claim 9 wherein said compound is 4,8-dimethyl-1,2,3,4,5,6-hexahydrobenzo[f]quinolin-3-one or a pharmaceutically acceptable salt thereof.

12. A formulation according to claim 9 wherein said compound is 8-methyl-1,2,3,4,5,6-hexahydrobenzo[f]quinolin-3-one or a pharmaceutically acceptable salt thereof.

13. A method for inhibiting 5α-reductase in mammals, which comprises administering to a mammal requiring 5α-reductase inhibition, a pharmaceutically effective amount of a compound of the Formula

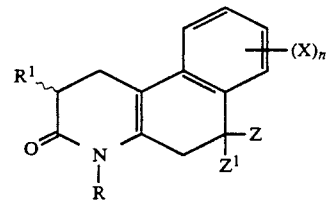

I where:
R is hydrogen, $C_1-C_4$ alkyl, unsubstituted or substituted phen($C_1-C_4$)alkyl;
Z and $Z^1$ are independently selected from hydrogen and $C_1-C_4$ alkyl;
$R^1$ is hydrogen or $C_1-C_4$ alkyl;
n is 1 or 2;
X is hydrogen, halogen, $NO_2$, cyano, $CF_3$, $C_1-C_6$ alkyl, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, mercapto, $C_1$-$C_6$ alkylthio, $C_1$-$C_6$ alkylsulfinyl, $C_1$-$C_6$ alkylsulfonyl, or a group —A—$R^2$ where A is $C_1$-$C_6$ alkylene, $C_2$-$C_6$ alkenylene or $C_2$-$C_6$ alkynylene; and $R^2$ is halogen, hydroxy, $CF_3$, $C_1$-$C_6$ alkoxy, carboxy, $C_1$-$C_6$ alkoxycarbonyl, amino, $C_1$-$C_4$ alkylamino, $C_1$-$C_4$ dialkylamino, amido, $C_1$-$C_4$ alkylamido, $C_1$-$C_4$ dialkylamido, $C_1$-$C_4$ alkylsulfonylamino, aminosulfonyl or $C_1$-$C_4$ alkylaminosulfonyl, and pharmaceutically acceptable salts thereof.

14. A method according to claim 13 where R is hydrogen or $C_1$-$C_4$ alkyl;

Z and $Z^1$ are independently hydrogen or methyl;

$R^1$ is hydrogen or methyl;

n is 1 or 2;

X is halogen, $CF_3$, $C_1$-$C_6$ alkyl, $C_1$-$C_4$ alkoxy or —A—$R_2$ where A is $C_1$-$C_4$ alkylene and $R_2$ is $C_1$-$C_4$ alkoxycarbonyl; and pharmaceutically acceptable salts thereof.

15. A method according to claim 14 where:

R is hydrogen or methyl;

Z and $Z^1$ are hydrogen or methyl;

$R^1$ is hydrogen or methyl;

n is 1 or 2;

X is halogen, $CF_3$, or $C_1$-$C_4$ alkyl; and pharmaceutically acceptable salts thereof.

16. A method according to claim 15 wherein said compound is 8-bromo-4-methyl-1,2,3,4,5,6-hexahydrobenzo[f]quinolin-3-one or a pharmaceutically acceptable salt thereof.

17. A method according to claim 15 wherein said compound is 4,8-dimethyl-1,2,3,4,5,6-hexahydrobenzo[f]quinolin-3-one or a pharmaceutically acceptable salt thereof.

18. A method according to claim 15 wherein said compound is 8-methyl-1,2,3,4,5,6-hexahydrobenzo[f]quinolin-3-one or a pharmaceutically acceptable salt thereof.

19. A method of treating benign prostatic hyperplasia in a mammal comprising administering to a mammal in need of treatment from benign prostatic hyperplasia, an effective amount of a compound of claim 1.

20. A method of treating benign prostatic hyperplasia in a mammal comprising administering to a mammal in need of treatment from benign prostatic hyperplasia, an effective amount of a compound of claim 2.

21. A method of treating benign prostatic hyperplasia in a mammal comprising administering to a mammal in need of treatment from benign prostatic hyperplasia, an effective amount of a compound of claim 3.

22. The method of claim 21 employing 8-bromo-4-methyl-1,2,3,4,5,6-hexahydrobenzo-[f]quinolin-3-one or a pharmaceutically acceptable salt thereof.

23. The method of claim 21 employing 4,8-dimethyl-1,2,3,4,5,6-hexahydrobenzo[f]quinolin-3-one or a pharmaceutically acceptable salt thereof.

24. The method of claim 21 employing 8-methyl-1,2,3,4,5,6-hexahydrobenzol[f]quinolin-3-one or a pharmaceutically acceptable salt thereof.

25. A method of treating hirsutism in a mammal comprising administering to a mammal in need of treatment from hirsutism, an effective amount of a compound of claim 1.

26. A method of treating hirsutism in a mammal comprising administering to a mammal in need of treatment from hirsutism, an effective amount of a compound of claim 2.

27. A method of treating hirsutism in a mammal comprising administering to a mammal in need of treatment from hirsutism, an effective amount of a compound of claim 3.

28. The method of claim 27 employing 8-bromo-4-methyl-1,2,3,4,5,6-hexahydrobenzo-[f]quinolin-3-one or a pharmaceutically acceptable salt thereof.

29. The method of claim 27 employing 4,8-dimethyl-1,2,3,4,5,6-hexahydrobenzo[f]quinolin-3-one or a pharmaceutically acceptable salt thereof.

30. The method of claim 27 employing 8-methyl-1,2,3,4,5,6-hexahydrobenzo[f]quinolin-3-one or a pharmaceutically acceptable salt thereof.

31. A method of treating acne vulgaris in a mammal comprising administering to a mammal in need of treatment from acne vulgaris, an effective amount of a compound of claim 1.

32. A method of treating acne vulgaris in a mammal comprising administering to a mammal in need of treatment from acne vulgaris, an effective amount of a compound of claim 2.

33. A method of treating acne vulgaris in a mammal comprising administering to a mammal in need of treatment from acne vulgaris, an effective amount of a compound of claim 3.

34. The method of claim 33 employing 8-bromo-4-methyl-1,2,3,4,5,6-hexahydrobenzo-[f]quinolin-3-one or a pharmaceutically acceptable salt thereof.

35. The method of claim 33 employing 4,8-dimethyl-1,2,3,4,5,6-hexahydrobenzo[f]quinolin-3-one or a pharmaceutically acceptable salt thereof.

36. The method of claim 33 employing 8-methyl-1,2,3,4,5,6-hexahydrobenzo[f]quinolin-3-one or a pharmaceutically acceptable salt thereof.

* * * * *